United States Patent [19]

Walker et al.

[11] 4,036,973
[45] July 19, 1977

[54] IMIDAZOL-1-YL PROPANE DERIVATIVES

[75] Inventors: Keith A. M. Walker, Palo Alto; Michael Marx, Sunnyvale, both of Calif.

[73] Assignee: Syntex (U.S.A.) Inc., Palo Alto, Calif.

[21] Appl. No.: 664,800

[22] Filed: Mar. 8, 1976

Related U.S. Application Data

[63] Continuation-in-part of Ser. No. 599,612, July 28, 1975, abandoned.

[51] Int. Cl.² .................. A61K 31/415; C07D 233/60
[52] U.S. Cl. .................................... 424/273; 260/309; 260/348 R; 260/609 F
[58] Field of Search ......................... 260/309; 424/273

[56] References Cited

U.S. PATENT DOCUMENTS

| | | | |
|---|---|---|---|
| 3,531,494 | 9/1970 | Adolphi et al. | 260/309 |
| 3,940,415 | 2/1976 | Buchel et al. | 260/309 |

*Primary Examiner*—Natalie Trousof
*Attorney, Agent, or Firm*—Alan M. Krubiner; William B. Walker

[57] ABSTRACT

Compounds of the formula

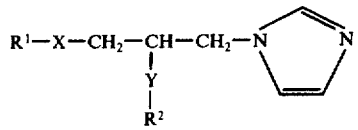

wherein one of $R^1$ and $R^2$ is alkyl or the group

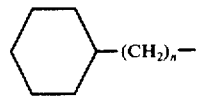

in which $n$ is 0 to 3 and the other of $R^1$ and $R^2$ is benzyl, substituted benzyl, phenyl or substituted phenyl, said substituted benzyl and substituted phenyl substituted on the phenyl ring with one or more substituents independently selected from the group consisting of halo, lower alkyl and trifluoromethyl; X and Y are independently oxygen or sulfur with the proviso that Y is not oxygen when $R^2$ is phenyl or substituted phenyl; and the antimicrobial acid addition salts thereof are useful as antifungal, antibacterial and antiprotozoal agents.

41 Claims, No Drawings

IMIDAZOL-1-YL PROPANE DERIVATIVES

RELATED APPLICATIONS

This case is a continuation-in-part of U.S. Ser. No. 599,612, filed July 28, 1975, now abandoned.

The present invention relates to novel chemical compounds which are derivatives of imidazole. More particularly, the present invention relates to compounds of the formula

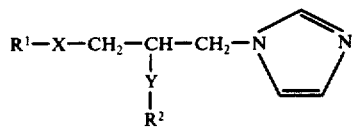

wherein:
one of $R^1$ and $R^2$ is alkyl or the group

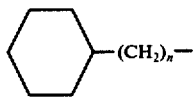

in which n is 0 to 3, and the other of $R^1$ and $R^2$ is benzyl, substituted benzyl, phenyl or substituted phenyl, said substituted benzyl and substituted phenyl substituted on the phenyl ring with one or more substituents independently selected from the group consisting of halo, lower alkyl and trifluoromethyl;

X and Y are independently oxygen or sulfur with the proviso that Y is not oxygen when $R^2$ is phenyl or substituted phenyl; and the antimicrobial acid addition salts thereof.

The term "alkyl" as used in the specification and appended claims refers to a saturated, unbranched or branched acyclic hydrocarbon group containing 1 to 12 carbon atoms such as methyl, ethyl, n-propyl, isopropyl, n-butyl, sec-butyl, isobutyl, tert-butyl, n-pentyl, n-hexyl, n-heptyl, n-octyl, n-nonyl, n-decyl, n-undecyl, n-dodecyl and the like. The term "lower alkyl" refers to an alkyl group as previously defined having 1 to 4 carbon atoms. The term "halo" refers to bromo, chloro and fluoro. The term "antimicrobial acid addition salts" refers to salts of the subject compounds which possess the desired activity and which are neither biologically nor otherwise undesirable. These salts are formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid and the like.

All compounds of Formula (I) possess at least one chiral center, i.e., the carbon atom to which are attached the $R^1XCH_2$, $R^2Y$, H and

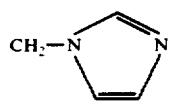

moieties. Accordingly, the compounds of the present invention may be prepared in either optically active form, or as a racemic mixture. Unless otherwise specified, the compounds described herein are all in the racemic form. However, the scope of the subject invention herein is not to be considered limited to the racemic form, but to encompass the individual optical isomers of the subject compounds.

If desired, racemic intermediates or final products prepared herein may be resolved into their optical antipodes by conventional resolution means known per se, for example, by the separation (e.g., fractional crystallization) of the diastereomeric salts formed by reaction of, e.g., racemic compounds of Formula (I) or the alcohol precursors of Formulas (1), (3) and (6) with an optically active acid, or by separation of the diastereometic esters formed by reaction of the racemic alcohol precursors of compounds of Formula (I) with an optically active acid. Exemplary of such optically active acids are the optically active forms of camphor-10-sulfonic acid, α-bromo-camphor-π-sulfonic acid, camphoric acid, menthoxy-acetic acid, tartaric acid, malic acid, diacetyltartaric acid, pyrrolidone-5-carboxylic acid and the like. The separated pure diastereomeric salts or esters may then be cleaved by standard means to afford the respective optical isomers of the compounds of Formula (I) or the precursor alcohols.

Alternatively, the subject compounds may be prepared in optically active form from optically active compounds of the formula

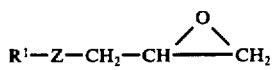

wherein Z is oxygen or sulfur.

The above compounds (15) are obtained from optically active forms of glycerol acetonide (2,2-dimethyl-1,1,3-dioxolane-4-methanol) by methods known in the art, e.g. J. Med. Chem. 1973, 16, pp. 168-169.

The subject compounds embraced by generic Formula (I) can be represented subgenerically as:

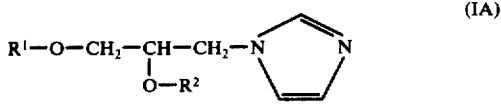

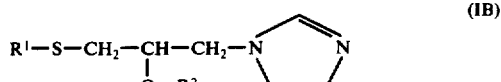

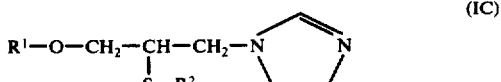

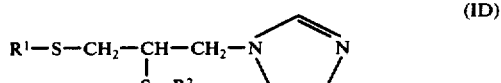

wherein:
one of $R^1$ and $R^2$ is alkyl or the group

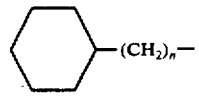

in which n is 0 to 3, and the other of R¹ and R² is benzyl, substituted benzyl, phenyl or substituted phenyl, said substituted benzyl and substituted phenyl substituted on the phenyl ring with one or more substituents independently selected from the group consisting of halo, lower alkyl and trifluoromethyl;

X and Y are independently oxygen or sulfur with the privso that Y is not oxygen when R² is phenyl or substituted phenyl; and the antimicrobial acid addition salts thereof.

Preferred compounds embraced by the above subgeneric Formulas are:

1. Compounds of Formulas (IA), (IB), (IC) and (ID) wherein R¹ is halo substituted benzyl or halo substituted phenyl and R² is alkyl;
2. Compounds of Formulas (IA) and (IB) wherein R¹ is alkyl and R² is halo substituted benzyl; and
3. Compounds of Formulas (IC) and (ID) wherein R¹ is is alkyl and R² is halo substituted benzyl or halo substituted phenyl.

Particularly preferred compounds within the group described in the previous paragraph are those wherein the halo substituted benzyl and halo substituted phenyl groups are 4-, 2,4-di- and 3,4-dichloro substituted benzyl and 4-, 2,4-di, 3,4-di, 2,4,5-tri, 2,4,6-tri and 2,3,4,5,6-pentachloro substituted phenyl and the alkyl group is a straight chain alkyl.

Especially preferred compounds within the group described in the previous paragraph are those having a 4-, 2,4-di- or 3,4-dichlorophenyl or a 4-, 2,4-di- or 3,4-dichlorobenzyl in combination with a straight chain alkyl having 3 to 8 carbon atoms.

The subject compounds of Formula (I) exhibit antifungal, antibacterial and antiprotozoal activity. For example, compounds of the present invention exhibit antifungal activity against human and animal pathogens such as

*Microsporum audouini,*
*Microsporum gypseum,*
*Microsporum gypseum - canis,*
*Epidermophyton floccosum,*
*Trichophyton mentagrophytes*
*Trichophyton rubrum,*
*Trichophyton tonsurans,*
*Candida albicans* and
*Cryptococcus neoformans.*

The compounds of the present invention also exhibit antifungal activity against fungi of primarily agricultural importance such as

*Aspergillus flavus,*
*Cladosporium herbarum,*
*Fusarium graminearum,*
*Penicillium notatum,*
*Aspergillus niger,*
*Penicillium oxalicum,*
*Penicillium spinulosum* and
*Pithomyces chartarum.*

In addition, the compounds of the present invention exhibit antibacterial activity against human and animal pathogens, such as mercaptan

*Staphylococcus aureus,*
*Streptococcus faecalis,*
*Corynebacterium acnes,*
*Erysipelothrix insidiosa,*
*Escherichia coli,*
*Proteus vulgaris,*
*Salmonella choleraesuis,*
*Pasteurella multocida* and
*Pseudomonas aeruginosa.*

Moreover, the compounds of the present invention exhibit antiprotozoal activity against protozoa such as *Trichomonas vaginalis.*

In view of the aforementioned activities, the subject compounds are found to be useful antimicrobials, having not only pharmaceutical but also agricultural and industrial application.

Accordingly, a further aspect of the present invention relates to compositions for pharmaceutical, agricultural and industrial use, which compositions comprise the subject compounds of Formula (I) in combination with a suitable carrier. A still further aspect of the present invention relates to methods of inhibiting the growth of fungi, bacteria and protozoa by applying to a host object containing, or subject to attack by, fungi, bacteria or protozoa an effective amount of a compound of the present invention or a suitable composition containing same.

In pharmaceutical applications, compositions may be solid, semi-solid or liquid in form such as tablets, capsules, powders, suppositories, liquid solutions, suspensions, creams, lotions, gels, ointments and the like. Pharmaceutically acceptable non-toxic carriers, or excipients normally employed for solid formulations include tricalcium phosphate, calcium carbonate, kaolin, bentonite, talcum, gelatin, lactose, starch and the like; for semi-solid formulations there may be mentioned, for example, polyalkylene glycols, vaseline and other cream bases; for liquid formulations there may be mentioned, for example, water, oils of vegetable origin and low boiling solvents such as isopropanol, hydrogenated naphthalenes and the like. The pharmaceutical compositions containing the compounds of the present invention may be subjected to conventional pharmaceutical expedients such as sterilization and can contain conventional pharmaceutical excipients such as preservatives, stabilizing agents, emulsifying agents, salts for the adjustment of osmotic pressure and buffers. The compositions may also contain other therapeutically active materials. In pharmaceutical applications, the subject compounds and compositions may be administered to humans and animals by conventional methods, e.g., topically, orally, parenterally and the like. Parenteral administration includes intramuscular as well as subcutaneous and intravenous injection. Intravenous injection of imidazole derivatives for certain systemic conditions has been demonstrated to be effective (see for example, Drugs, 9, 419–420 (1975), which described the intravenous administration of Miconazole, i.e., 1-[2,4-dichloro-β-(2',4'-dichlorobenzyloxy)phenethyl]imidazole nitrate, to patients with systemic candidiasis).

Topical application is the preferred method of administration in pharmaceutical applications. For such treatment, an area having an existing fungal, bacterial or protozoal growth, or to be protected against attack by fungi, bacteria or protozoa may be treated with the subject compounds or compositions by, for example, dusting, sprinkling, spraying, rinsing, brushing, dipping, smearing, coating, impregnating and the like. Topical compositions containing the compounds of the present invention exhibit antifungal, antibacterial and antiprotozoal activity over a wide range of concentration, for example, from about 0.1 to 10.0% by weight of the composition.

The pharmaceutical compositions hereof typically comprise one or more subject compounds of Formula (I) and a pharmaceutically acceptable, non-toxic carrier, and are preferably formulated in unit dosage form to facilitate administration (unit dosage being the amount of active ingredient administered on one occasion).

In general, for systemic (e.g. oral or parenteral) administration it is expedient to administer the active ingredient in amounts of between about 1 and 100 mg./kg. body weight per day (preferably between about 5 and 50 mg./kg. body weight per day) distributed over several applications (e.g. in 3 individual doses) in order to achieve effective results. For localized (e.g. topical) administration however, proportionately less of the active ingredient is required. The exact regimen for pharmaceutical administration of the compounds and compositions disclosed herein will necessarily be dependent upon the needs of the individual subject being treated, the type of treatment, e.g., whether preventative or curvative, the type of organism involved and, of course, the judgment of the attending practitioner. In any event the compositions to be administered will contain a quantity of the subject compound in an amount effective for relief or prevention of the specific condition being treated.

In agricultural applications, the subject compounds may be applied directly to plants (e.g., seeds, foliage) or to soil. For example, compounds of the present invention may be applied to seeds alone or in admixture with a powdered solid carrier. Typical powdered carriers are the various mineral silicates, e.g., mica, talc, pyrophyllite and clays. The subject compounds may also be applied to the seeds in admixture with a conventional surface-active wetting agent with or without additional solid carrier. Surface-active wetting agents that can be used are any of the conventional anionic, non-anionic or cationic types. As a soil treatment for fungi and the like, the subject compounds can be applied as a dust in admixture with sand, soil or a powdered solid carrier such as a mineral silicate with or without additional surface-active agent, or the subject compounds can be applied as an aqueous spray optionally containing a surface-active dispersing agent and a powdered solid carrier. As a foliage treatment, the subject compounds may be applied to growing plants as an aqueous spray which contains a surface-active dispersing agent with or without a powdered solid carrier and hydrocarbon solvents.

In industrial applications, the subject compounds may be used to control bacteria and fungi by contacting the pathogens with the compounds in any known manner. Materials capable of supporting bacteria and fungi may be protected by contacting, mixing or impregnating these materials with the subject compounds. In order to increase their effectiveness, the subject compounds may be combined with other pesticidal control agents such as fungicides, bactericides, insecticides, miticides and the like. A particularly important industrial/agricultural use for the subject compounds of the present invention is as a food preservative against bacteria and fungi which cause deterioration and spoilage of foods.

DETAILED DESCRIPTION

The present invention in a still further aspect is directed to methods for the preparation of the subject compounds of Formula (I).

Sequence 1

The following reaction sequence, directed to the preparation of compounds of Formulas (IA) and (IB), can be illustrated as follows:

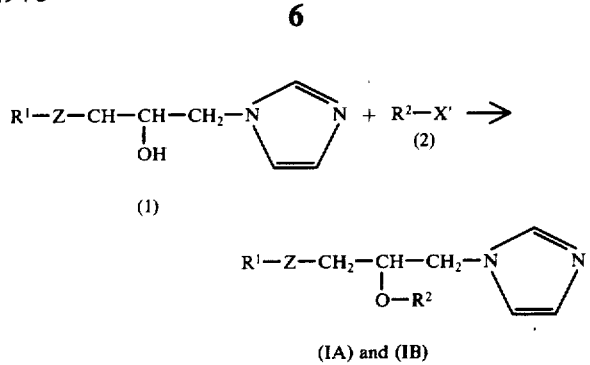

wherein $R^1$ is as previously defined, $R^2$ is limited to alkyl,

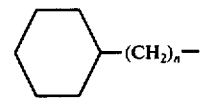

in which $n$ is 0 to 3, benzyl or substituted benzyl, Z is oxygen or sulfur, and X' is a conventional leaving group such as a halide (e.g., bromide or chloride), or a sulfonate ester (e.g., methanesulfonate or p-toluenesulfonate).

In the above sequence, the imidazole derivatives of Formulas (IA) and (IB) are prepared by converting a hydroxy compound of Formula (1) to its metal salt by treatment with a strong base, such as sodium hydride and the like, and thereafter contacting the resulting metal salt with a compound of Formula (2). Preparation of the metal salt is effected in an organic solvent such as hexamethylphosphoramide, tetrahydrofuran, dimethylformamide and the like, at a temperature of 0° to 65° C. for a period of 30 minutes to 4 hours. Thereafter, reaction of the metal salt with a compound of Formula (2) is carried out, preferably, in the same solvent at a temperature of 0° to 65° C. for a period of 1 to 24 hours.

Sequence 2

The following reaction sequence, directed to the preparation of compounds of Formula (IC), can be illustrated as follows:

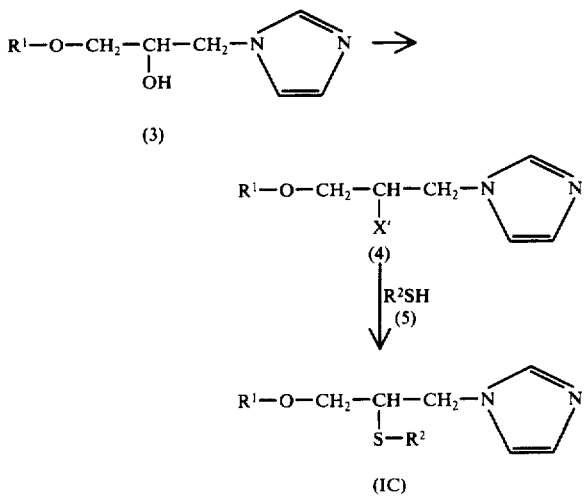

wherein $R^1$ and $R^2$ are as previously defined and X' is a conventional leaving group such as a halide (e.g., chloride or bromide) or a sulfonate ester (e.g., methanesulfonate or p-toluenesulfonate).

In the above sequence, the imidazole derivatives of Formula (IC) are prepared from compounds of Formula (3) by a two-step sequence involving conversion of the hydroxy group to a suitable leaving group followed by reaction with a metal salt of a thiol of Formula (5).

The conversion of an alcohol of Formula (3) to a compound of Formula (4) is carried out by means well known in the art. For example, the alcohol may be halogenated using a halogenating agent such as thionyl chloride or thionyl bromide, either neat, or in a inert organic solvent such as dichloromethane or chloroform, at a temperature between about 0° to 80° C., preferably between about 20° and 80° C. The halogenation reaction may be carried out in the presence of a molar equivalent of a base (e.g., pyridine) if desired. Alternative halogenation procedures include, for example, the use of triphenylphosphine with either carbon tetrachloride, carbon tetrabromide, or N-chloro (or N-bromo)-succinimide. When utilizing thionyl chloride or thionyl bromide without the use of added base, the hydrochloride or hydrobromide salt of the corresponding halo compound is produced. This salt is preferably neutralized (e.g., with potassium carbonate) prior to its use in the thioalkylation step, however the salt may be used directly if excess thiol salt or base is utilized.

Sulfonate esters may be prepared by the standard proedure of treating the alcohol with an excess of, for example, methanesulfonyl chloride or p-toluenesulfonyl chloride, in the presence of a base, for example, pyridine or triethylamine. This reaction is carried out at a temperature from about −20° to +50° C., preferably between about 0° and 20° C.

The thus prepared compounds of Formula (4) are then treated with a metal salt, preferably an alkali metal salt such as the sodium or potassium salt, of a thiol of Formula (5) in the presence of an inert organic solvent at a temperature from about 20° to about 80° C.

The reaction of compounds of Formula (4) with compounds of Formula (5) wherein $R^2$ in Formula (5) is alkyl,

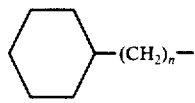

in which $n$ is 0 to 3, benzyl or substituted benzyl is carried out in an inert organic solvent such as tetrahydrofuran, ether, methanol and the like in the presence of a suitable base such as sodium hydride or sodium methoxide at a temperature of 20° to 67° C. for a period of 30 minutes to 24 hours.

The reaction of compounds of Formula (4) with compounds of Formula (5) wherein $R^2$ in Formula (5) in phenyl or substituted phenyl is carried out in an inert organic solvent such as acetone, methanol and the like in the presence of a suitable base such as potassium carbonate, sodium hydroxide or sodium methoxide at ambient temperature to reflux for a period of 30 minutes to 72 hours.

Sequence 3

The following reaction sequence, directed to the preparation of compounds of Formula (ID), can be illustrated as follows:

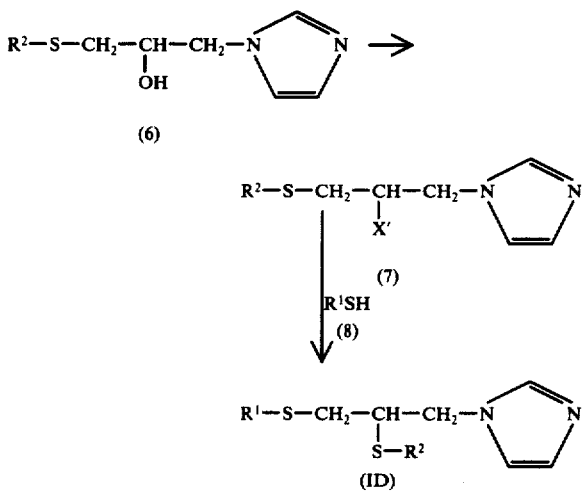

wherein $R^1$ and $R^2$ are as previously defined and $X'$ is a conventional leaving group such as a halide (e.g. chloride or bromide), or a sulfonate ester (e.g. methanesulfonate or p-toluenesulfonate).

In the above sequence, the compounds of Formula (7) are prepared in the same manner previously described for the preparation of compounds of Formula (4) in Sequence 2.

Thereafter the imidazole derivatives of Formula (ID) are prepared by treating a compound of Formula (7) with a metal salt, preferably an alkali metal salt such as the sodium or potassium salt of a thiol of Formula (8) in the presence of an inert organic solvent at a temperature of 20° to 80° C. This particular reaction proceeds via a cyclic intermediate with the net result being attachment of the entering $R^1$-S-moiety at the —$CH_2$-position and the migration of the original $R^2$-S-moiety from this position to the —CH= position.

The reaction of compounds of Formula (7) with compounds of Formula (8) wherein $R^1$ in Formula (8) is alkyl,

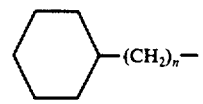

in which $n$ is 0 to 3, benzyl or substituted benzyl is carried out as previously described in the preparation of compounds of Formula (IC) in Sequence 2 (see paragraph 6).

The reaction of compounds of Formula (7) with compounds of Formula (8) is phenyl or substituted phenyl, is carried out as previously described in the preparation of compounds of Formula (IC) in Sequence 2 (see paragraph 7).

Sequence 4

The following reaction sequence, directed to a second method for the preparation of compounds of Formula (IC), can be illustrated as follows:

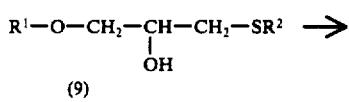

(9)

$$R^1-O-CH_2-CH-CH_2-SR^2$$
$$\phantom{R^1-O-CH_2-CH}|$$
$$\phantom{R^1-O-CH_2-CHH}X'$$

(10)

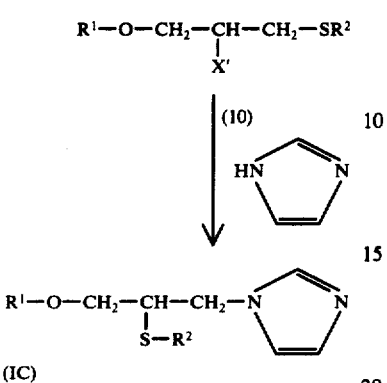

(IC)

wherein R¹ and R² are as previously described and X' is a conventional leaving group such as a halide (e.g. chloride or bromide) or a sulfonate ester (e.g. methanesulfonate or p-toluenesulfonate.

In the above sequence, compounds of Formula (10) are prepared in the manner previously described for the preparation of compounds of Formula (4) in Sequence 2.

Thereafter, compounds of Formula (10) are reacted with imidazole in an organic solvent such as acetonitrile, dimethylformamide and the like to obtain the imidazole derivatives of Formula (IC). This reaction is carried out at a temperature of 0° to 100° C. for a period of 1 to 24 hours.

The subject compounds of the instant invention can be isolated as free bases, however, since many of the compounds in base form are oils or gums, it is more convenient to isolate and characterize the compounds as acid addition salts. These salts are prepared in the usual manner, i.e., by reaction of the base compound with a suitable inorganic or organic acid, described above. Salts formed with dibasic acids (e.g. oxalic acid) may contain one or two molecules of base per molecule of acid. All oxalates described herein contain one molecule of oxalic acid per molecule of imidazole base. If desired, the salts can be readily converted to the compounds in base form by treatment with alkali, such as potassium carbonate, sodium carbonate or sodium or potassium hydroxide.

The alcohols required as starting materials for preparation of the subject compounds of the instant invention are either available or can be obtained by known processes.

For example, the alcohols required in Sequences 1-3 can be prepared as follows:

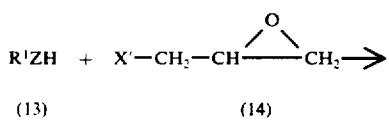

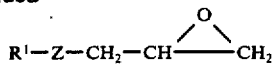

(15)

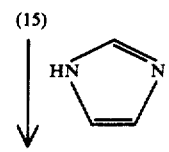

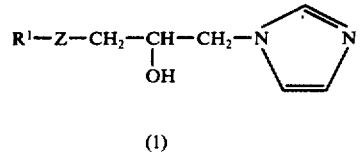

(1)

wherein R¹ is as previously defined, X' is chloro or bromo and Z is oxygen or sulfur.

In the above depicted sequence, the 2,3-epoxypropyl (thio)ethers of Formula (15) are prepared by reaction of a compound of Formula (13) with an epihalohydrin such as epichlorohydrin or epibromohydrin followed by reaction of the resulting 2,3-epoxypropyl (thio) ether with imidazole.

The reaction of compounds of Formula (13) with epihalohydrins, wherein R¹ in Formula (13) is alkyl, $$\underset{}{\bigcirc}-(CH_2)_n-$$

in which n is 0 to 3, benzyl or substituted benzyl is carried out in an inert organic solvent such as tetrahydrofuran, ether and the like in the presence of a suitable base such as sodium hydride at a temperture of 0° to 67° C. for a period of 30 minutes to 72 hours.

The reaction of compounds of Formula (13) with epihalohydrins, wherein R¹ in Formula (13) is phenyl or substituted phenyl is carried out in an inert organic solvent such as acetone, methanol and the like in the presence of a suitable base such as potassium carbonate, sodium hydroxide and sodium methoxide at ambient temperature to reflux for a period of 30 minutes to 24 hours.

The thus obtained 2,3-epoxypropyl (thio) ethers of Formula (15) are then reacted with at least one molar equivalent of imidazole (preferably an excess) in an inert organic solvent such as acetonitrile, dimethylformamide, and the like, at a temperature of 0° to 80° C. for a period of 1 to 72 hours to obtain the alcohols of Formula (1).

When R¹ is a small alkyl group such as methyl, ethyl etc., in alcohols of Formula (1), such alcohols tend to be relatively water soluble. In such cases, variations necessary in the reaction and work up procedures will be apparent to those skilled in the art. Such variations may include use of a low boiling organic solvent, non-aqueous work up, chromatographic separation, removal of excess imidazole at a later stage, etc.

The above discussion particularly applies to certain alcohols prepared in Preparations A and B on pages 21 to 24.

Alcohols required in Sequence 4 can be prepared as follows:

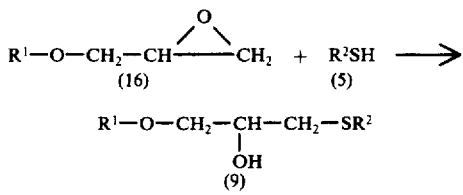

wherein R¹ and R² are as previously defined.

In the above depicted sequence, the alcohols of Formula (9) are prepared by reaction of a 2,3-epoxypropyl ether of Formula (16) with a thiol of Formula (5).

The reaction of a 2,3-epoxypropyl ether (16) with a compound of Formula (5) wherein R² in Formula (5) is alkyl,

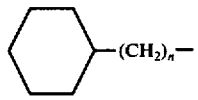

in which n is 0 to 3, benzyl or substituted benzyl is carried out in a solvent such as tetrahydrofuran, ether, methanol and the like in the presence of a suitable base such as sodium hydride or sodium methoxide at ambient temperature to reflux for a period of 30 minutes to 24 hours.

The reaction of 2,3-epoxypropyl ether (16) with a compound of Formula (5) wherein R² in Formula (5) is phenyl or substituted phenyl is carried out in an inert organic solvent such as acetone, methanol and the like in the presence of a suitable base such as potassium carbonate, sodium hydroxide and sodium methoxide at ambient temperature to reflux for a period of 30 minutes to 24 hours.

DESCRIPTION OF SPECIFIC EMBODIMENTS

The following specific description is given to enable those skilled in the art to more clearly understand and practice the present invention. It should not be considered as a limitation upon the scope of the invention but merely as being illustrative and representative thereof.

Preparation A

A 56% dispersion of sodium hydride in mineral oil (2.2 g.) is added at room temperature to a solution of 7.95 g. of 4-chlorobenzylmercaptan in 100 ml. of dry tetrahydrofuran. The resulting salt is then treated with 6.9 g. epibromohydrin in 20 ml. tetrahydrofuran and the mixture stirred for 30 minutes and evaporated to dryness. Thereafter, 250 ml. of ether is added to the residue and the ether extract washed with water. The organic phase is dried over magnesium sulfate and evaporated; excess epibromohydrin being removed under vacuum. To the resulting oil is added 17 g. imidazole and 50 ml. dimethylformamide. The mixture is stirred overnight at 60° C. and then poured into water and the aqueous phase extracted with ether. The resulting product is chromatographed on silica gel and eluted with 10% methanol in methylene chloride to yield 12.3 g. of 1-[3'-(4''-chlorobenzylthio)-2'-hydroxypropyl] imidazole as an amber gum.

Similarly, replacing 4-chlorobenzyl mercaptan in the above procedure with equipment amounts of other suitable thiols or alcohols is productive of the following 1-[3'-R¹-thio(oxy)-2'-hydroxypropyl]imidazoles:

1-[3'-methylthio-2'-hydroxypropyl]imidazole,
1-[3'-ethylthio-2'-hydroxypropyl]imidazole,
1-[3'-isopropylthio-2'-hydroxypropyl]imidazole,
1-[3'-n-propylthio-2'-hydroxypropyl]imidazole,
1-[3'-n-butylthio-2'-hydroxypropyl]imidazole,
1-[3'-n-hexylthio-2'-hydroxypropyl]imidazole,
1-[3'-n-penthylthio-2'-hydroxypropyl]imidazole,
1-[3'-n-octylthio-2'-hydroxypropyl]imidazole,
1-[3'-n-nonylthio-2'-hydroxypropyl]imidazole,
1-[3'-n-decylthio-2'-hydroxypropyl]imidazole, 1-[3'-n-dodecylthio-2'-hydroxypropyl]imidazole,
1-[3'-cyclohexylthio-2'-hydroxypropyl]imidazole,
1-[3'-cyclohexylmethylthio-2'-hydroxypropyl]imidazole,
1[3'-benzylthio-2'-hydroxypropyl]imidazole,
1-[3'-(3''-bromobenzylthio)-2'-hydroxypropyl]imidazole,
1-[3'-(4''-bromobenzylthio)-2'-hydroxypropyl]imidazole,
1-[3'-(2'',4''-dichlorobenzylthio)-2'-hydroxypropyl]imidazole,
1-[3'-(3'',4''-dichlorobenzylthio)-2'-hydroxypropyl]imidazole,
1-[3'-(4''-fluorobenzylthio)-2'-hydroxypropyl]imidazole,
1[3'-(3'-methylbenzylthio-2'-hydroxypropyl]imidazole,
1-[3'-(4''-methylbenzylthio)-2'-hydroxypropyl]imidazole,
1-[3'-(2'',4'',6''-trimethylbenzylthio)-2'-hydroxypropyl]imidazole,
1-[3'-(4''t-butylbenzylthio)-2'-hydroxypropyl]imidazole,
1[3'-(4''-trifluoromethylbenzylthio)-2'-hydroxypropyl]imidazole
1-[3'-methoxy-2'-hydroxypropyl]imidazole,
1[3'-n-propoxy-2'-hydroxypropyl]imidazole,
1[3'-isopropoxy-2'-hydropypropyl]imidazole,
1-[3'-t-butoxy-2'-hydroxypropyl]imidazole,
1-[3'-n-pentyloxy-2'-hydroxypropyl]imidazole,
1-[3'-n-hexyloxy-2'-hydroxypropyl]imidazole,
1-[3'-n-heptyloxy-2'-hydroxypropyl]imidazole,
1-[3'-n-decyloxy-2'-hydroxypropyl]imidazole,
1-[3'-n-dodecyloxy-2'-hydroxypropyl]imidazole,
1-[3'-(3-cyclohexyl-n-propoxy)-2'-hydroxypropyl]imidazole,
1-[3'-benzyloxy-2'-hydroxypropyl]imidazole,
1-[3'-(4''-chlorobenzyloxy)-2'-hydroxypropyl]imidazole,
1-[3'-(4''-bromobenzyloxy)-2'-hydroxypropyl]imidazole,
1[3'-(4''-fluorobenzyloxy)-2'-hydroxypropyl]imidazole,
1-3'-(4''-trifluromethylbenzyloxy)-2'-hydroxypropyl]imidazole
1-[3'n-noctyloxy-2-hydroxypropyl]imidazole, and
1-[3'-n-nonyloxy-2-hydroxypropyl]imidazole.

Preparation B

A mixture of 3.8 g. of 2,4-dichlorothiophenol, 5.5 g. of epibromohydrin and 5.6 g. of anhydrous potassium carbonate in 100 ml. acetone is stirred at reflux. After 2 hours the mixture is evaporated to dryness and 100 ml. of water is added to the residue. The resultant aqueous mixture is extracted with ether and the ether extract washed with water. The organic phase is dried over magnesium sulfate and evaporated to yield a pale yellow oil.

Without further purification the oil obtained above is added to 7.0 g. of imidazole in 15 ml. dimethylformamide. After stirring for 3 days at 25° C. the reaction mixture is poured into water. The product is extracted with ether and the ether extracts filtered, washed with water, dried over magnesium sulfate and evaporated. The residue is chromatographed on silica gel eluting with 10% methanol in dichloromethane to yield 1-[3'-(2'',4''-dichlorophenylthio)-2'-hydroxypropyl]imidazole as a pale yellow gum which solidifies.

Similarly, replacing 2,4-dichlorothiophenol in the above procedure with other thiophenols or phenols is productive of the following 1-[3'-phenylthio (oxy)-2'-hydroxypropyl]imidazoles:

1-[3'-phenylthio-2'-hydroxypropyl]imidazole,
1-[3'-(4''-chlorophenylthio)-2'-hydroxypropyl]imidazole,
1-[3'-(3'',4''-dichlorophenylthio)-2'-hydroxypropyl]imidazole,
1-[3'-pentachlorophenylthio-2'-hydroxypropyl]imidazole,
1-[3'-(4''-bromophenylthio)-2'-hydroxypropyl]imidazole,
1-[3'-(3''-bromophenylthio)-2'-hydroxypropyl]imidazole,
1-[3'-(4''-fluorophenylthio)-2'-hydroxypropyl]imidazole,
1-[3'-(4''-trifluoromethylphenylthio)-2'-hydroxypropyl]imidazole,
1-[3'-(3''-methylphenylthio)-2'-hydroxypropyl]imidazole,
1-[3'-(4''-t-butylphenylthio)-2'-hydroxypropyl]imidazole,
1-[3'-phenoxy-2'-hydroxypropyl]imidazole,
1-[3'-(4''-chlorophenoxy)-2'-hydroxypropyl]imidazole, 1-[3'-(2'',4''-dichlorophenoxy)-2'-hydroxypropyl]imidazole,
1-[3'-(3'',4''-dichlorophenoxy)-2'-hydroxypropyl]imidazole,
1-[3'-pentachlorophenoxy-2'-hydroxypropyl]imidazole,
1-[3'-(4''-bromophenoxy)-2'-hydroxypropyl]imidazole,
1-[3'-(2'',4'',6''-trimethylphenoxy)-2'-hydroxypropyl]imidazole,
1-[3'-(4''-t-butylphenoxy)-2'-hydroxypropyl]imidazole,
1-[3'-(3''-trifluoromethylphenoxy)-2'-hydroxypropyl]imidazole
1-[3'-(2'',4''-dibromophenoxy)-2'-hydroxypropyl]imidazole,
1-[3'-(2'',4''-dibromophenylthio-2'-hydroxypropyl]imidazole,
1-[3'-(2'',4''-difluorophenoxy)-2'-hydroxypropyl]imidazole, and
1-[3'-(2'',4''-difluorophenylthio)-2'-hydroxypropyl]imidazole.

Preparation C 2,4-Dichlorophenyl 2,3-epoxypropyl ether (2.2 g.) in several ml. of dry tetrahydrofuran is added with stirring to a prereacted mixture of 1.5 g. of n-heptylthiol and 50 mg. of sodium hydride (56% dispersion in mineral oil) in 40 ml. tetrahydrofuran. The mixture is then stirred at 55° C. for 6 hours. The solvent is then removed from the reaction mixture and 30 ml. of water is added to the residue. The resulting aqueous mixture is extracted with ether and the ether extracts washed with water, dried over magnesium sulfate and evaporated to yield 3-(2',4'-dichlorophenoxy)-1-(n-heptylthio)-2-propanol.

Similarly, replacing 2,4-dichlorophenyl 2,3-epoxypropyl ether in the above procedure with equivalent amounts of other suitable 2,3-epoxypropyl ethers and/or replacing n-heptylthiol with other suitable thiols is productive of the following 3-($R^1$-oxy)-1-($R^2$-thio)-2-propanols:

3-methoxy-1-(4'-t-butylbenzylthio)-2-propanol,
3-n-butoxy-1-(2',4'-dichlorobenzylthio)-2-propanol,
3-n-pentyloxy-1-(4'-chlorobenzylthio)-2-propanol,
3-n-pentyloxy-1-(2',4'-dichlorobenzylthio)-2-propanol,
3-n-hexyloxy-1-(4'-chlorobenzylthio)-2-propanol,
3-n-hexyloxy-1-(2',4'-dichlorobenzylthio)-2-propanol,
3-n-hexyloxy-1-(3',4'-dichlorobenzylthio)-2-propanol,
3-n-heptyloxy-1-(4'-chlorobenzylthio)-2-propanol,
3-n-heptyloxy-1-(3',4'-dichlorobenzylthio)-2-propanol,
3-n-heptyloxy-1-(2',4'-dichlorobenzylthio)-2-propanol,
3-n-octyloxy-1-(4'-chlorobenzylthio)-2-propanol, 3-n-octyloxy-1-(4'-bromobenzylthio)-2-propanol,
3-n-octyloxy-1-(4'-trifluoromethylbenzylthio)-2-propanol,
3-n-nonyloxy-1-(4'-chlorobenzylthio)-2-propanol,
3-n-decyloxy-1-(pentafluorobenzylthio)-2-propanol,
3-n-dodecyloxy-1-benzylthio-2-propanol,
3-cyclohexylmethoxy-1-(2',4',6'-trimethylbenzylthio)-2-propanol,
3-benzyloxy-1-decylthio-2-propanol,
3-(4'-chlorobenzyloxy)-1-n-octylthio-2-propanol,
3-(4'-chlorobenzyloxy)-1-n-nonylthio-2-propanol,
3-(4'-bromobenzyloxy)-1-n-octylthio-2-propanol,
3-(4'-fluorobenzyloxy)-1-n-nonylthio-2-propanol,
3-pentamethylbenzyloxy-1-n-butylthio-2-propanol,
3-(4'-t-butylbenzyloxy)-1-n-hexylthio-2-propanol,
3-(3'-trifluoromethylbenzyloxy)-1-n-octylthio-2-propanol,
3-phenoxy-1-n-dodecylthio-2-propanol,
3-(4'-chlorophenoxy)-1-n-pentylthio-2-propanol,
3-(4'-chlorophenoxy)-1-n-hexylthio-2-propanol,
3-(4'-chlorophenoxy)-1-n-heptylthio-2-propanol,
3-(4'-chlorophenoxy)-1-n-octylthio-2-propanol,
3-(4'-chlorophenoxy)-1-n-nonylthio-2-propanol,
3-(2',4'-dichlorophenoxy)-1-n-butylthio-2-propanol,
3-(2',4'-dichlorophenoxy)-1-n-pentylthio-2-propanol,
3-(2',4'-dichlorophenoxy)-1-n-hexylthio-2-propanol,
3-(2',4'-dichlorophenoxy)-1-n-octylthio-2-propanol,
3-(3',4'-dichlorophenoxy)-1-n-hexylthio-2-propanol,
3-(3',4'-dichlorophenoxy)-1-n-heptylthio-2-propanol,
3-(3',4'-dichlorophenoxy)-1-n-octylthio-2-propanol,
3-pentachlorophenoxy-1-methylthio-2-propanol,
3-pentachlorophenoxy-1-n-propylthio-2-propanol,
3-pentachlorophenoxy-1-isobutylthio-2-propanol,
3-(4'-chloro-3'-trifluoromethylphenoxy)-1-n-heptylthio-2-propanol,
3-(4'-bromophenoxy)-1-n-octylthio-2-propanol,
3-(2',4',6'-tribromophenoxy)-1-n-pentylthio-2-propanol,
3-(3'-fluorophenoxy)-1-n-dodecylthio-2-propanol,
3-(4'-t-butylphenoxy)-1-n-hexylthio-2-propanol,
3-(4'-t-butylphenoxy)-1-cyclohexylthio-2-propanol and
3-(2',6'-dimethyl-4'-t-butylphenoxy)-1-n-butylthio-2-propanol.

Preparation D 2,3-Epoxypropyl isopropyl ether (1.16 g.), 3.2 g. of pentachlorothiophenol and 1.5 g. of potassium carbonate in 50 ml. of acetone are stirred at reflux overnight. The solvent is then removed and water is added to the residue. The resultant aqueous phase is then extracted with ether and the ether extracts washed with water, dried over magnesium sulfate and evaporated to dryness to yield crude 3-isopropoxy-1-pentachlorophenylthio-2-propanol.

EXAMPLE 1

A 56% dispersion of sodium hydride in mineral oil (480 mg.) is added under nitrogen to a solution of 2.52 g. of 1-[3'-(4''-chlorophenoxy)-2'-hydroxypropyl]imidazole in 6 ml. dry hexamethylphosphoramide. After stirring for 1 hours at room temperature, the temperature is increased to 45° C. and stirring is continued for 2 hours. The solution is then cooled in an ice bath and 2.5 g. of 1-bromodecane in 1 ml. of hexamethylphosphoramide is added. Thereafter, the solution is stirred for 2 hours at room temperature and then for 16 hours at 50° C. The reaction mixture is poured into water and the resultant aqueous mixture extracted with ether and the ether extracts washed with water. The organic phase is dried over magnesium sulfate and evaporated. The resulting residue is chromatographed on silica gel. Elution with 20% acetone in dichloromethane yields 1-[3'-(4''-chlorophenoxy)-2'-(n-decyloxy)propyl]imidazole.

An ethereal solution of the above obtained base is acidified with ethereal oxalic acid yielding, after recrystallization of the crude salt from ethyl acetate, 1-[3'-(4''-chlorophenoxy)-2'-(n-decyloxy)propyl]imidazole oxalate.

EXAMPLE 2

Thionyl chloride (5 ml.) and 1.6 g. of 1-[3'-(n-decyloxy)-2'-hydroxypropyl]imidazole are warmed gently for a period of 2 hours and the solution is then evaporated to dryness. The residue is dissolved in dichloromethane and rendered basic with aqueous potassium carbonate solution. The organic layer is separated, dried over magnesium sulfate and evaporated to yield 1-[2'-chloro-3'-(n-decyloxy)propyl]imidazole.

The chloro compound obtained above, i.e., 1-[2'-chloro-3'-(n-decyloxy)propyl]imidazole (1.6 g.) is then stirred and heated under reflux with 1.1 g. of thiophenol and 1.2 g. anhydrous potassium carbonate in 40 ml. of acetone. After stirring for approximately 16 hours the solvent is removed and water is added to the residue. The resultant aqueous phase is then extracted with ether and the ether extracts washed with water, dried over magnesium sulfate and evaporated to yield 1-[3'-(n-decyloxy)-2'-(phenylthio)propyl]imidazole.

An ethereal solution of the above obtained base is acidified with ethereal oxalic acid yielding, after recrystallization of the crude salt from ethyl acetate, 1-[3'-(n-decyloxy)-2'-(phenylthio)propYl]imidazole oxalate.

EXAMPLE 3

1-[3'-(4''-chlorobenzylthio)-2'-hydroxypropyl]imidazole (500 mg.) and 0.5 ml. of thionyl chloride in 20 ml. dichloromethane are warmed gently for ½ hour. Thereafter, the reaction mixture is evaporated to yield a gum which is dissolved in 50 ml. dichloromethane and basified with aqueous potassium carbonate solution. The organic phase is separated, dried over magnesium sulfate and evaporated.

The chloro compound obtained above is dissolved in 5 ml. of tetrahydrofuran and added to the salt formed in situ from 600 mg. of n-hexyl mrcaptan and 200 mg. of sodium hydride (56% dispersion in mineral oil) in 30 ml. tetrahydrofuran. The mixture is stirred overnight at room temperature and then evaporated to dryness. To the residue is added 30 ml. of water and the resultant aqueous phase is then extracted with 100 ml. of ether.

The ether extract is washed with water, dried over magnesium sulfate and evaporated to dryness. The residue is chromatographed on silica gel. Elution with 5% acetone in dichloromethane yields 1-[2'-(4''-chlorobenzylthio)-3'-(n-hexylthio)]imidazole as a gum.

Acidification of an ethereal solution of the above obtained gum with ethereal oxalic acid yields, after recrystallization from ethyl acetate, 1-[2'-(4''-chlorobenzylthio)-3-(n-hexylthio)propyl]imidazole oxalate, m.p. 130°–131°C.

EXAMPLE 4

1-[3'-n-octylthio-2'-hydroxypropl]imidazole (2.7 g.) and 3 ml. of thionyl chloride in 50 ml. dichloromethane are warmed gently for 2 hours and the solution is then evaporated to dryness. The resulting residue is dissolved in 150 ml. dichloromethane and rendered basic with aqueous potassium carbonate solution. The organic layer is separated, dried over magnesium sulfate and evaporated.

The chloro compound obtained above is then heated under reflux with 1.75 g. of p-chlorothiophenol and 1.6 g. of potassium carbonate in 100 ml. of acetone. After stirring for approximately 4 hours at reflux the solvent is removed from the reaction mixture and water is added to the residue. The resultant aqueous phase is extracted with ether and the ether extracts washed with water, dried over magnesium sulfate and evaporated. The residue is chromatographed on silica gel. Elution with 10% acetone in dichloromethane yields 1-[3'-(4''-chlorophenylthio)-2'-n-octylthio)propyl]imidazole.

EXAMPLE 5

3-(2'',4''-dichlorophenoxy)-1-(n-heptylthio)-2-propanol (3.5 g.) in 30 ml. of dichloromethane and 3 ml. of thionyl chloride are stirred for 2 hours at room temperature. Thereafter the solution is evaporated to dryness and 10 ml. of acetonitrile and 4 g. of imidazole are added to the resulting residue. The reaction mixture is then stirred overnight at room temperature and then at 60° C. for 24 hours. The solvent is removed and 30 ml. of water is added to the resulting residue. The resulting aqueous phase is then extracted with ether and the ether extracts washed with water, dried over magnesium sulfate and evaporated to yield 1-[3'-(2'',4''-dichlorophenoxy)-2'-(n-heptylthio)-propyl]imidazole.

An ethereal solution of the above obtained base is acidified with oxalic acid yielding, after recrystallization of the crude salt from ethyl acetate, 1-[3'-(2'',4''-dichlorophenoxy)-2-(n-heptylthio)propyl]imidazole, oxalate.

EXAMPLE 6

Crude 3-isopropoxy-1-pentachlorophenylthio-2-propanol, obtained in Preparation D, in 60 ml. of dichloromethane and 5 ml. of thionyl chloride are stirred for 2 hours at room temperature. The solution is then evaporated to dyrness and 5 ml. of acetonitrile and 4 g. of imidazole are added to the resulting residue. The reaction mixture is stirred at 80° C for 48 hours and then evaporated to dryness. To the resulting residue is added 30 ml. of water. The resultant aqueous phase is extracted with ether and the ether extracts washed with water, dried over magnesium sulfate and evaporated to yield crude 1-[3'-isopropoxy-2'-(pentachlorophenylthio)propyl]imidazole.

An ethereal solution of the above obtained base is acidified with nitric acid yielding, after recrystallization of the crude salt from ethyl acetate, 1-[3'-isopropoxy-2'-(pentachlorophenylthio)propyl]imidazole nitrate, m.p. 126°–129° C. (decomp.).

EXAMPLE 7

Repeating the procedure in paragraph 1 of Example 1 using reactants of Formulas (1) and (2) as dictated by the particular 1-{3'-[R$^1$-oxy(thio)]-2'-[-R$^2$-oxy]propyl}imidazole desired is productive of the following compounds as free bases, which where indicated, are further characterized by conversion to the indicated acid addition salt, by treatment in the conventional manner with the appropriate acid:

1-[2'-(n-decyloxy)-3'-(2",4",6"-trimethylphenoxy)-propyl]-imidazole, oxalate salt, m.p. 88°–89° C.,
1-[2'-(n-dodecyloxy)-3'-(phenoxy)propyl]imidazole,
1-[3'-(4"-bromophenoxy)-2'-(n-decyloxy)propyl]imidazole,
1-[2'-(4"-bromobenzyloxy)-3'-(n-decyloxy)propyl]imidazole,
1-[2'-(n-hexyloxy)-3'-(pentachlorophenoxy)propyl]imidazole,
1-[3'-(2",4"-dichlorophenoxy)-2'-(n-nonyloxy)propyl]imidazole,
1-[3"-(3",4"-dichlorophenoxy)-2'-(n-nonyloxy)-propyl]imidazole, oxalate salt, m.p. 109.5°–110° C.,
1-[3'-(4"-chlorobenzyloxy)-2'-(n-decyloxy)propyl]imidazole,
1-[2'-(4"-chlorobenzyloxy)-3'-(n-decyloxy)propyl]imidazole,
1-[3'-(methoxy)-2'-(pentamethylbenzyloxy)propyl]imidazole,
1-[2'-(2",4",5"-trichlorobenzyloxy)-3'-(n-heptyloxy)propyl]imidazole,
1-[2'-benzyloxy)-3'-(n-dodecyloxy)propyl]imidazole,
1-[2'-(4"-t-butylbenzyloxy)-3'-(3-cyclohexyl-n-propoxy)-propyl]imidazole,
1-[3'-(benzyloxy)-2'-(n-dodecyloxy)propyl]imidazole,
1-[2'-(n-dodecyloxy)-3'-(4"-fluorobenzyloxy)propyl]imidazole,
1-[2'-(n-decyloxy)-3'-(4"-bromobenzyloxy)propyl]imidazole,
1-[2'-(n-decyloxy)-3'-(4"-trifluoromethylbenzyloxy)-propyl]imidazole,
1-[3'-(4"-t-butylphenoxy)-2'-(3-cyclohexyl-n-propoxy)propyl]imidazole,
1-[2'-(n-octyloxy)-3'-(3"-trifluoromethylphenoxy)-propyl]imidazole
1-[3'-(n-decyloxy)-2'-(4'-trifluoromethylbenzyloxy)-propyl]imidazole,
1-[2'-(methoxy)-3'-(pentachlorophenoxy)propyl]imidazole,
1-[2'-(n-butoxy)-3'-(pentachlorophenoxy)propyl]imidazole,
1-[2'-(4"-fluorobenzyloxy)-3'-(n-dodecyloxy)propyl]imidazole,
1-[2'-(cyclohexylethoxy)-3'-(2",4"-dichlorophenylthio)propyl]imidazole,
1-[2'-(n-butoxy)-3'-(pentachlorophenylthio)propyl]imidazole,
1-[2'-(3",4"-dichlorobenzyloxy)-3'-(cyclohexylthio)propyl]imidazole,
1-[2'-(benzyloxy)-3'-(n-dodecylthio)propyl]imidazole,
1-[2'-(n-octyloxy)-3'-(2",4"-dichlorophenylthio)-propyl]imidazole,
1-[2'-(n-octyloxy)-3'-(3",4"-dichlorophenylthio)-propyl]imidazole,
1-[2'-(3",4"-dichlorobenzyloxy)-3'-(n-heptylthio)-propyl]imidazole,
1-[3'-(4"-chlorophenylthio)-2'-(n-nonyloxy)propyl]imidazole,
1-[3'-(4"-chlorophenylthio)-2'-(n-decyloxy)propyl]imidazole,
1-[3'-(4"-chlorobenzylthio)-2'-(n-octyloxy)propyl]imidazole,
1-[3'-(4"-chlorobenzylthio)-2'-(n-nonyloxy)propyl]imidazole,
1[2'-(4"-chlorobenzyloxy)-3'-(n-octylthio)propyl]imidazole,
1-[2'-(4"-chlorobenzyloxy)-3'-(n-nonylthio)propyl]imidazole,
1-[3'-(2",4"-dichlorobenzylthio)-2'-(n-heptyloxy)-propyl]imidazole,
1-[3'-(3",4"-dichlorobenzylthio)-2'-(n-heptyloxy)-propyl]imidazole,
1-[2'-(2",4"-dichlorobenzyloxy)-3'-(n-heptylthio)proply]imidazole,
1-[3'-(methylthio)-2'-(pentamethylbenzyloxy)propyl]imidazole,
1-[3'-(n-butylthio)-2'-(2",4",5"-trichlorobenzyloxy)-propyl]imidazole,
1-[3'-(benzylthio)-2'-(n-decycloxy)propyl]imidazole,
1-[3'-(4"-bromobenzylthio)-2'-(n-octyloxy)propyl]imidazole,
1-[3'-(4"-fluorobenzylthio)-2'-(n-decyloxy)propyl]imidazole,
1-[2'-(n-heptyloxy)-3'-(2",4",6"-trimethylbenzylthio)-propyl]imidazole,
1-[2'-(n-octyloxy)-3'-(4"-trifluoromethylbenzylthio)-propyl]imidazole,
1-[2'-(n-dodecyloxy)-3'-(phenylthio)propyl]imidazole,
1-[3'-(4"-bromophenylthio)-2'-(n-nonyloxy)propyl]imidazole,
1-[3'-(4"-fluorophenylthio)-2'-(n-decyloxy)propyl]imidazole,
1-[2'-(n-nonyloxy)-3'-(4"-trifluoromethylphenylthio)-propyl]imidazole,
1-[2'-(methoxy)-3'-(pentachlorophenylthio)propyl]imidazole,
1-[2'-(4"-bromobenzyloxy)-3'-(n-octylthio)propyl]imidazole,
1-[2'-(4"-fluorobenzyloxy)-3'-(n-decylthio)propyl]imidazole,
1-[2'-t-butylbenzyloxy)-3'-(n-hexylthio)propyl]imidazole,
1-[2'-(t-butylbenzyloxy)-3'-(cyclohexylmethylthio)-propyl]imidazole,
1-[3'-(2",4"-dichlorophenoxy)-2'-(n-octyloxy)propyl]imidazole,
1-[3'-(2",4"-dichlorophenoxy)-2'-(n-decyloxy)propyl]imidazole,
1-[2'-(3",4"-dichlorobenzyloxy)-3'-(n-octyloxy)-propyl]imidazole, 1-[2'-(3",4"-dichlorobenzyloxy)-3'-(n-nonyloxy)-propyl]imidazole,
1-[2'-(3",4"-dichlorobenzyloxy)-3'-(n-decyloxy)-propyl]imidazole,
1-[2'-(2",4"-dichlorobenzyloxy)-3'-(n-octyloxy)-propyl]imidazole,
1-[2'-(2",4"-dichlorobenzyloxy)-3'-(n-nonyloxy)-propyl]imidazole,
1-[2'-(2",4"-dichlorobenzyloxy)-3'-(n-decyloxy)-propyl]imidazole,
1-[3'-(3",4"-dichlorophenoxy)-2'-(n-octyloxy)propyl]imidazole,
1-[3'-(3", 4"-dichlorophenoxy)-2'-(n-nonyloxy)-propyl]imidazole,
1-[3'-(3",4"-dichlorophenoxy)-2'-(n-decyloxy)propyl]imidazole,
1-[2'-(4"-chlorobenzyloxy)-3'(n-decyloxy)propyl]imidazole,
1-[3'-(2",4"-dichlorophenylthio)-2'-(n-nonyloxy)-propyl]imidazole,
1-[2'-(3", 4"-dichlorobenzyloxy)-3'-(n-octylthio)-propyl]imidazole,
1-[2'-(2",4"-dichlorobenzyloxy)-3'-(n-hexylthio)-propyl]imidazole,
1-[2'-(2", 4"-dichlorobenzyloxy)-3'-(n-octylthio)-propyl]imidazole,
1-[3'-(2",4"-dichlorophenylthio)-2'-(n-hexyloxy)-propyl]imidazole,
1-[3'-(3",4"-dichlorophenylthio)-2'-(n-heptyloxy)-propyl]imidazole,
1-[3'-(3",4"-dichlorophenylthio)-2'-(n-nonloxy)propyl]imidazole,
1-[3'-(4"-chlorophenylthio)-2'-(n-pentyloxy)propyl]imidazole,
1-[3'-(4"-chlorophenylthio)-2'-n-hexyloxy)propyl]imidazole,
1-[3'-(4"-chlorophenoxy)-2'-(n-hexyloxy)propyl]imidazole,
1-[3'-(4"-chlorophenoxy)-2'-(n-heptyloxy)propyl]imidazole,
1-[3'-(4"-chlorophenoxy)-2'-(n-octyloxy)propyl]imidazole,
1-[3'-(2",4"-dichlorophenoxy)-2'-(n-pentyloxy)-propyl[imidazole,
1-[3'-(2",4"dichlorophenoxy)-2'-(n-hexyloxy)propyl]imidazole,
1-[3'-(2",4"-dichlorophenoxy)-2"-(n-heptyloxy)-propyl]imidazole,
1-[3'-(4"-chlorophenylthio)-2'-(n-heptyloxy)-propyl]imidazole,
1-[3'-(2",4"-dichlorophenylthio)-2'-(n-pentyloxy)-propyl]imidazole,
1-[3'-(4"-chlorobenzylthio)-2'-(n-pentyloxy)propyl]imidazole,
1-[3'-chlorobenzylthio)-2'-(n-hexyloxy)propyl]imidazole,
1-[3'-(4"-chlorobenzylthio)-2'-(n-heptyloxy)propyl]
1-[3'-(n-butylthio)-2'-(4"-chlorobenzyloxy)propyl]imidazole,
1-[2'-(4"-chlorobenzyloxy)-3'-(n-pentylthio)propyl]imidazole,
1-[2'-(4"-chlorobenzyloxy)-3'-(n-hexylthio)propyl]imidazole,
1-[2'-(4"-chlorobenzyloxy)-3'-(n-pentyloxy)propyl]imidazole,
1-[2'-(4"-chlorobenzyloxy)-3'-(n-hexyloxy)-propyl]imidazole,
1-[2'-(4"-chlorobenzyloxy)-3'-(n-heptyloxy)propyl]imidzole,
1 -[2'-(2",4"-dichlorobenzyloxy)-3'-n-propylthio)-propyl]imidazole,
1-[3'-(n-butylthio)-2'-(2",4"-dichlorobenzyloxy)-propyl]imidazole,
1-[2'-(2",4"-dichlorobenzyloxy)-3'-(n-pentylthio)-propyl]imidazole,
1-[3'-(n-butoxy)-2'-(2",4"-dichlorobenzyloxy)propyl]imidazole,
1[2'-(2",4"-dichlorobenzyloxy)-3'-(n-pentyloxy)-propyl]imidazole and
1-[2'-(2",4"-dichlorobenzyloxy)-3'-(n-hexyloxy)-propyl]imidazole.

EXAMPLE 8

Repeating the procedure in paragraphs 1 and 2 of Example 2 using reactants of Formulas (3) and (5) as dictated by the particular 1-[3'-($R^1$-oxy)-2'-($R^2$-thio)-propyl]imidazole desired is productive of the following compounds as free bases:

1[3'-(n-decyloxy)-2'-(4"-fluorophenhlthio)propyl]imidazole,
1-[3'-(n-decyloxy)-2'-(3"-methylphenylthio)propyl]imidazole,
1-[3'-(isopropoxy)-2'-(pentachlorophenylthiopropyl]imidazole,
1-[3'-(n-propoxy)-2'-(pentachlorophenylthiopropyl]imidazole,
1-[3'-(t-butoxy)-2'-(pentachlorophenylthiopropyl]imidazole,
1-[2'-(2",4"-dichlorophenylthio)-3'-(n-heptyloxy)-propyl]imidazole,
1-[2'-(3",4'-dichlorophenylthio)-3'-(n-heptyloxy)-propyl]imidazole,
1-[2'-(4"-chlorophenylthio)-3'-(n-octyloxy)propyl]imidazole,
1-[2'-(4"-chlorophenylthio)-3'-(n-nonyloxy)propyl]imidazole,
1-[3'-(methoxy)-2'-(pentachlorophenylthio)propyl]imidazole,
1-[3'-(n-dodecyloxy)-2'-(phenylthio)propyl]imidazole,
1-[3'-(3'-cyclohexyl-n-propoxy)-2'-(3",4"-dichlorophenylthio)propyl]imidazole,
1-[2'-(4"-chlorophenylthio)-3'-(n-decyloxy)propyl]imidazole,
1-[2'-(3",4"-dichlorophenylthio)-3'-(n-octyloxy)-propyl]imidazole,
1-[2'-(2",4"-dichlorophenylthio)-3'-(n-octyloxy)-propyl]imidazole,
1-[2'-(4"-chlorophenylthio)-3'-(n-pentyloxy)propyl]imidazole,
1-[2'-(4"-chlorophenylthio)-3'-(n-hexyloxy)propyl]imidazole,
1-[2'-(4"-chlorophenylthio)-3'-(n-heptyloxy)propyl]imidazole,
1-[3'-(n-butoxy)-2'-(2",4"-dichlorophenylthio)propyl]imidazole,
1-[2'-(2",4"-dichlorophenylthio)-3'-(n-pentyloxy)-propyl]imidazole,
1-[2'-(2",4"-dichlorophenylthio)-3'-(n-hexyloxy)-propyl]imidazole,
1-[3'-(n-butoxy)-2'-(3",4"-dichlorophenylthio)propyl]imidazole,
1-[2'-(3",41-dichlorophenylthio)-2'-(n-pentyloxy)-propyl]imidazole and 1-[2'-(3'',4''-dichlorophenylthio)-2'-(n-hexyloxy)-propyl]imidazole.

EXAMPLE 9

Repeating the procedure in paragraphs 1-3 of Example 3 using reactants of Formulas (6) and (8) as dictated by the particular 1-[2'-(R²-thio)-3'-(R¹-thio)propyl]imidazole desired is productive of the following compounds as free bases, which where indicated, are further characterized by conversion to the indicated acid addition salt, by treatment in the conventional manner with the appropriate acid:

1-[3'-(4''-chlorobenzylthio)-2'-(n-heptylthio)propyl]imidazole,
1-[3'-(benzylthio)-2'-(n-octylthio)propyl]imidazole,
1-[3'-(n-octylthio)-2'-(benzylthio)propyl]imidazole,
1-[3'-(methylthio)-2'-(4''-t-butylbenzylthio)propyl]imidazole,
1-[2'-(3'',4''-dichlorophenylthio)-3'-(n-hexylthio)propyl]imidazole,
1-[3'-(4''-chlorobenzylthio)-2'-(n-hexylthio)propyl]imidazole,
1-[2'-(2'',4''-dichlorophenylthio)-3'-(n-pentylthio)propyl]imidazole,
1-[2'-(3'',4''-dichlorophenylthio)-3'-(n-pentylthio)propyl]imidazole,
1-[2'-(4''-chlorobenzylthio)-3'-cyclohexylthio)propyl]imidazole, oxalate salt, m.p. 128.5°-131° C.,
1-[2'-(pentachlorophenylthio)-3'-(ethylthio)propyl]imidazole,
1-[2'-(pentachlorophenylthio)-3'-(isopropylthio)propyl]imidazole,
1-[2'-(2'',4''-dichlorophenylthio)-3'-(n-hexylthio)propyl]imidazole, oxalate salt, m.p 91.5°-93° C.,
1-[2'-(4''-chlorophenylthio)-3'-(n-heptylthio)propyl]imidazole,
1-[2'-(4''-chlorophenylthio)-3'-(n-octylthio)propyl]imidazole,
1-[2'-(4''-chlorobenzylthio)-3'-(n-heptylthio)propyl]imidazole,
1-[3'-(n-dodecylthio)-2'-(phenylthio)propyl]imidazole,
1-[3'-(2''-bromobenzylthio)-2'-(cyclohexylmethylthio)propyl]imidazole,
1-[3'-(4''-fluorobenzylthio)-2'-(n-heptylthio)propyl]imidazole,
1-[3'-(2'',4'',6''-trimethylbenzylthio)-2'-(n-pentylthio)propyl]imidazole,
1-[2'-(n-butylthio)-3'-(4''-t-butylbenzylthio)propyl]imidazole,
1-[2'-(n-hexylthio)-3'-(3''-trifluoromethylbenzylthio)propyl]imidazole,
1-[2'-(4''-bromobenzylthio)-3'-(n-hexylthio)propyl]imidazole,
1-[2'-(4''-fluorobenzylthio)-3'-(n-octylthio)propyl]imidazole,
1-[3'-(n-heptylthio)-2'-(4''-methylbenzylthio)propyl]imidazole,
1-[3'-(n-hexylthio)-2'-(4''-trifluoromethylbenzylthio)propyl]imidazole,
1-[2'-(3''-bromophenylthio)-3'-(n-heptylthio)propyl]imidazole,
1-[2'-(4''-fluorophenylthio)-3'-(n-nonylthio)propyl]imidazole,
1-[2'-(3''-methylphenylthio)-3'-(n-octylthio)propyl]imidazole,
1-[2'-(n-butylthio)-3'-(4''-chlorobenzylthio)propyl]imidazole,
1-[3'-(4''-chlorobenzylthio)-2'-(n-pentylthio)propyl]imidazole,
1-[3'-(n-butylthio)-2'-(4''-chlorophenylthio)propyl]imidazole,
1-[2'-(4''-chlorophenylthio)-3'-(n-pentylthio)propyl]imidazole,
1-[2'-(4''-chlorophenylthio)-3'-(n-hexylthio)propyl]imidazole,
1-[2'-(2'',4''-dichlorophenylthio)-3'-(n-propylthio)propyl]imidazole,
1-[3'-(n-butylthio)-2'-(2'',4''-dichlorophenylthio)propyl]imidazole,
1-[2'-(3'',4''-dichlorophenylthio)-3'-(n-propylthio)propyl]imidazole,
1-[3'-(n-butylthio)-2'-(3'',4''-dichlorophenylthio)propyl]imidazole,
1-[3'-(n-butylthio)-2'-(4''-chlorobenzylthio)propyl]imidazole,
1-[2'-(4''-chlorobenzylthio)-3'-(n-pentylthio)propyl]imidazole,
1-[2'-(2'',4''-dichlorobenzylthio)-3'-(n-propylthio)propyl]-imidazole,
1-[3'-(n-butylthio(-2'-(2',4''-dichlorobenzylthio(propyl]-imidazole and
1-[2'-(2'',4''-dichlorobenzylthio)-3'-(n-pentylthio)propyl]-imidazole.

EXAMPLE 10

Repeating the procedure of Example 4 using reactants of Formulas (6) and (8) as dictated by the particular 1-[2'-(R²-thio)-3'-(R¹-thio)propyl]imidazole desired is productive of the following compounds as free bases:

1-[3'-(4''-chlorophenylthio)-2'-(n-heptylthio)propyl]imidazole,
1-[3'-(pentachlorophenylthio)-2'-(methylthio)propyl]imidazole,
1-[3'-(3'',4''-dichlorophenylthio)-2'-(n-hexylthio)propyl]imidazole,
1-[3'-(2'',4''-dichlorophenylthio)-2'-(n-pentylthio)propyl]imidazole,
1-[3'-(3'',4''-dichlorophenylthio)-2'-(n-pentylthio)propyl]imidazole,
1-[3'-(pentachlorophenylthio)-2'-(ethylthio)propyl]imidazole,
1-[3'-(pentachlorophenylthio)-2'-(isopropylthio)propyl]imidazole,
1-[3'-(2'',4''-dichlorophenylthio)-2'-(n-hexylthio)propyl]imidazole,
1-[2'-(n-dodecylthio)-3'-(phenylthio)propyl]imidazole,
1-[3'-(3''-bromophenylthio)-2'-(n-heptylthio)propyl]imidazole,
1-[3'-(4''-fluorophenylthio)-2'-(n-nonylthio)propyl]imidazole,
1-[2'-(n-butylthio)-3'-(4''-t-butyl-2''-methylphenylthio)propyl]imidazole,
1-[3'-(4''-chlorophenylthio)-2'-(n-pentylthio)propyl]imidazole,
1-[3'-(4''-chlorophenylthio)-2'-(n-hexylthio)propyl]imidazole and
1-[2'-(n-butylthio)-3'-(2'',4''-dichlorophenylthio)propyl]imidazole.

EXAMPLE 11

Repeating the procedure in paragraph 1 of Example 5 using reactants of Formula (9) as dictated by the particular 1-[3'-(R¹-oxy)-2'-(R²-thio)propyl]imidazole desired is productive of the following compounds as free bases, which where indicated, are further characterized by conversion to the indicated acid addition salt, by treatment in the conventional manner with the appropriate acid:

1-[3'-(4''-chlorobenzyloxy)-2'-(n-nonylthio)propyl]imidazole, 1-[3'-(4''-t-butylphenoxy)-2'-(cyclohexylthio)propyl]imidazole,
1-[3'-(4''-chlorophenoxy)-2'-(n-nonylthio)propyl]imidazole,
1-[3'-(pentachlorohenoxy)-2'-(n-propylthio)propyl]imidazole,
1-[3'-(pentachlorophenoxy)-2'-isobutylthio)propyl]imidazole,
1-[3'-(3''4''-dichlorophenoxy)-2'-(n-heptylthio)propyl]imidazole,
1-[3'-(4''-chlorophenoxy)-2'-(n-octylthio)propyl]imdiazole,
1-[3'-(4''-chlorobenzyloxy)-2'-(n-octylthio)propyl]imidazole,
1-[2''-chlorobenzylthio)-3'-(n-octyloxy)propyl]imidazole,
1[2'-(4''-chlorobenzylthio-3'-(n-nonyloxy)propyl]imidazole,
1-[2'-(4''-t-butylbenzylthio)-3'-(methoxy)propyl]imidazole, 1- [2'-(3'',4''-dichlorobenzylthio)-3'-(n-hexyloxy)- propyl]imidazole,
1-[2'-(benzylthio)-3'-(n-dodecyloxy)propyl]imidazole,
1-[3'-(cyclohexylmethoxy)-2'-(2'',4'',6''-trimethylbenzylthio)propyl]imidazole,
1-[3'-(benzyloxy)-2'-(n-decylthio)propyl]imidazole,
1-[3'-(4''-fluorobenzyloxy)-2'-(n-nonylthio)propyl]imidazole,
1-[3'-(4''-bromobenzyloxy)-2'-(n-octylthio)propyl]imidazole,
1-[2'-(n-butylthio-3'-(pentamethylbenzyloxy)propyl]imidazole,
1-[3'-(4''-t-butylbenzyloxy)-2'-(n-hexylthio)propyl]imidazole,
1-[2'-(n-octylthio-3'-(3'''-trifluoromethylbenzyloxy)propyl]imidazole,
1-[2'-(n-dodecylthio)-3'-(phenoxy)propyl]imidazole,
1-[3'-(2'',4'',6''-tribromophenoxy-2-n-pentylthio)propyl]imidazole,
1-[2'-(n-dodecylthio)-3'-(3''-fluorophenoxy)propyl]imidazole,
1-[2'-butylthio)-3'-(2'',6''-dimethyl-4''-t-butylphenoxy)propyl]imidazole,
1-[2'-(n-heptylthio)-3'-(4''-chloro-3''-trifluoromethylphenoxy)propyl]imidazole,
1-[2'-(methylthio)-3'-(pentachlorophenoxy)propyl]imidazole,
1-[3'-(n-decyloxy)-2'-(pentafluorobenzylthio)propyl]imidazole,
1-[2'-(4''-bromobenzylthio)-3'-(n-octyloxy)propyl]imidazole,
1-[3'-(n-octyloxy)-2'-(4''-trifluoromethylbenzylthiopropyl]imidazole,
1-[3'-(2'',4''-dichlorophenoxy)-2'-(n-hexylthio)propyl]imidazole,
1-[3'-(2'',4''-dichlorophenoxy)-2'-(n-heptylthio)propyl]imidazole,
1-[3'-(2'',4''-dichlorophenoxy)-2'-(n-octylthio)propyl]imidazole,
1-[2'-(3'',4''-dichlorobenzylthio)-3'-(n-heptyloxy)propyl]imidazole,
1-[2'-(2'',4''-dichlorobenzylthio)-3'-(n-heptyloxy)propyl]imidazole,
1-[3'-(3'',4''-dichlorophenoxy)-2'-(n-hexylthio)propyl]imidazole,
1-[3'-(3'',4''-dichlorophenoxy)-2'-(n-octylthio)propyl]imidazole,
1-[3'-(4''-t-butylphenoxy)-2'-(n-hexylthio)propyl]imidazole, oxalate salt, m.p. 106°-107.5° C.,
1-[3'-(4''-bromophenoxy)-2'-(n-octylthio)propyl]imidazole, oxalate salt, m.p. 88.5°-92.5° C.,
1-[3'-(4''-chlorophenoxy)-2'-(n-pentylthio)propyl]imidazole,
1-[3'-(4''-chlorophenoxy)-2'-(n-hexylthio)propyl]imidazole,
1-[3'-(4''-chlorophenoxy)-2'-(n-heptylthio)propyl]imidazole,
1-[2'-(n-butylthio)-3'-(2'',4''-dichlorophenoxy)propyl]-imidazole,
1-[3'-(2'',4''-dichlorophenoxy)-2'-(n-pentylthio)propyl]-imidazole,
1-[2'-(4''-chlorobenzylthio)-3'-(n-pentyloxy)propyl]imidazole,
1-[2'-(4''-chlorobenzylthio)-3'-(n-hexyloxy)propyl]imidazole,
1-[2'-(4''-chlorobenzylthio)-3'-(n-heptyloxy)propyl]imidazole,
1-[3'-(n-butoxy)-2'-(2'',4''-dichlorobenzylthio)propyl]-imidazole,
1-[2'-(2'',4''-dichlorobenzylthio)-3'-(n-pentyloxy)propyl]-imidazole and
1-[2'-(2'',4''-dichlorobenzylthio)-3'-(n-hexyloxy)propyl]-imidazole.

EXAMPLE 12

1-[2'-(4''-chlorobenzylthio)-3'-(n-hexylthio)propyl]imidazole oxalate (2.3 g.) in 100 ml. of dichloromethane is shaken with excess potassium carbonate solution until the salt is completely dissolved. The organic layer is then separated, washed with water, dried over magnesium sulfate and evaporated to yield 1-[2'-(4''-chlorobenzylthio)-3'-(n-hexylthio)propyl]imidazole.

In similar manner, the antimicrobial acid addition salts of all compounds of formula (I) can be converted to the corresponding compounds in base form.

EXAMPLE 13

Nitric acid (70%; $d = 1.42$) is added dropwise to a stirred solution of 2.0 g. of 1-[3'-isopropoxy-2'-(pentachlorophenylthio)propyl]imidazole in 30 ml. of anhydrous ether until precipitation was complete. The product was filtered off, washed with ether, air dried, and recrystallized from ethyl acetate to yield 1-[3'-isopropoxy-2'-(pentachlorophenylthio)propyl]imidazole nitrate.

In similar manner, all compounds of Formula (I) in base form can be converted to the antimicrobial acid addition salts by treatment with the appropriate acid, for example, hydrochloric acid, hydrobromic acid, sulfuric acid, nitric acid, phosphoric acid, acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid or p-toluenesulfonic acid.

EXAMPLE 14

The following example illustrates the preparation of representative formulations containing an active compound, such as a salt of 1-[2'-(4''-chlorobenzylthio)-3-(n- hexylthio)propyl]-imidazole which may be used for controlling fungi, bacteria and protozoa.

A. Topical Formulation

| | grams |
|---|---|
| Active compound | 0.2 – 2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA(butylated hydroxy anisole) | 0.01 |
| Water          qs | 100 |

All of the above ingredients, except water, are combined and heated at 60° C. with stirring. A sufficient quantity of water at 60° C. is then added with vigorous stirring to provide 100 g. of the cream formulation which is then cooled to room temperature.

B. I.V. Formulation

| | | |
|---|---|---|
| Active compound | 0.5 | g. |
| Propylene glycol | 20 | g. |
| Polyethylene glycol 400 | 20 | g. |
| Tween 80 | 1 | g. |
| 0.9% Saline solution    qs | 100 | ml. |

The active compound is dissolved in propylene glycol, polyethylene glycol 400 and Tween 80. A sufficient quantity of 0.9% saline solution is then added with stirring to provide 100 ml. of the I.V. solution which is filtered through a 0.2 micron membrane filter and packaged under sterile conditions.

C. Oral Formulation

| | parts by weight |
|---|---|
| Active compound | 200 |
| Magnesium stearate | 3 |
| Starch | 30 |
| Lactose | 116 |
| PVP (polyvinylpyrrolidone) | 3 |

The above ingredients are combined and granulated using methanol as the solvent. The formulation is then dried and formed into tablets (containing 200 mg. of active compound) with an appropriate tabletting machine.

What is claimed is:

1. A compound of the formula:

$$R^1-X-CH_2-CH(Y-R^2)-CH_2-N\text{(imidazole)} \quad (I)$$

wherein:
one of $R^1$ and $R^2$ is alkyl having 1 to 12 carbon atoms or the group $$\text{(cyclohexyl/phenyl)}-(CH_2)_n-$$

in which $n$ is 0 to 3, and the other of $R^1$ and $R^2$ is benzyl, substituted benzyl, phenyl or substituted phenyl, said substituted benzyl and substituted phenyl substituted on the phenyl ring with one or more substituents independently selected from the group consisting of halo, lower alkyl and trifluoromethyl;

X and Y are independently oxygen or sulfur with the proviso that Y is not oxygen when $R^2$ is phenyl or substituted phenyl; and the antimicrobial acid addition salts thereof.

2. A compound of claim 1 wherein X and Y are oxygen.

3. A compound of claim 1 wherein X is sulfur and Y is oxygen.

4. A compound of claim 1 wherein X is oxygen and Y is sulfur.

5. A compound of claim 1 wherein X and Y are sulfur.

6. A compound of claim 1 selected from the group consisting of:
   a. those wherein $R^1$ is halo substituted benzyl or halo substituted phenyl and $R^2$ is alkyl;
   b. those wherein $R^1$ is alkyl and $R^2$ is halo substituted benzyl; or
   c. those wherein $R^1$ is alkyl, $R^2$ is halo substituted phenyl and Y is sulfur.

7. A compound of claim 6 wherein halo substituted benzyl or halo substituted phenyl group is 4-, 2,4-di- or 3,4-dichloro substituted benzyl or 4-, 2,4-di- or 3,4-dichloro substituted phenyl and the alkyl group is a straight chain alkyl having 3 to 8 carbon atoms.

8. The compound of claim 7 which is 1-[3'-(4''-chlorophenoxy)-2'-(n-pentylthio)propyl]imidazole and the antimicrobial acid addition salts thereof.

9. The compound of claim 7 which is 1-[3'-(4''-chlorophenoxy)-2'-(n-hexylthio)propyl]imidazole and the antimicrobial acid addition salts thereof.

10. The compound of claim 7 which is 1-[3'-(4''-chlorophenoxy)-2'-(n-heptylthio)propyl]imidazole and the antimicrobial acid addition salts thereof.

11. The compound of claim 7 which is 1-[3'-(4''-chlorophenoxy)-2'-(n-hexyloxy)propyl]imidazole and the antimicrobial acid addition salts thereof.

12. The compound of claim 7 which is 1-[3'-(4''-chlorophenoxy)-2'-(n-heptyloxy)propyl]imidazole and the antimicrobial acid addition salts thereof.

13. The compound of claim 7 which is 1-[3'-(4''-chlorophenoxy)-2'-(n-octyloxy)propyl]imidazole and the antimicrobial acid addition salts thereof.

14. The compound of claim 7 which is 1-[2'-(n-butylthio)-3'-(2'',4''-dichlorophenoxy)propyl]imidazole and the antimicrobial acid addition salts thereof.

15. The compound of claim 7 which is 1-[3'-(2'',4''-dichlorophenoxy)-2'-(n-pentylthio)propyl]imidazole and the antimicrobial acid addition salts thereof.

16. The compound of claim 7 which is 1-[3'-(2'',4''-dichlorophenoxy)-2'-(n-hexylthio)propyl]imidazole and the antimicrobial acid addition salts thereof.

17. The compound of claim 7 which is 1-[3'-(2'',4''-dichlorophenoxy)-2'-(n-pentyloxy)propyl]imidazole and the antimicrobial acid addition salts thereof.

18. The compound of claim 7 which is 1-[3'-(2'',4''-dichlorophenoxy)-2'-(n-hexyloxy)propyl]imidazole and the antimicrobial acid addition salts thereof.

19. The compound of claim 7 which is 1-[3'-(2'',4''-dichlorophenoxy)-2'-(n-heptyloxy)propyl]imidazole and the antimicrobial acid addition salts thereof.

20. The compound of claim 7 which is 1-[3'-(4''-chlorophenylthio)-2'-(n-pentylthio)propyl]imidazole and the antimicrobial acid addition salts thereof.

21. The compound of claim 7 which is 1-[3'-(4''-chlorophenylthio)-2'-(n-hexylthio)propyl]imidazole and the antimicrobial acid addition salts thereof.

22. The compound of claim 7 which is 1-[3'-(4''-chlorophenylthio)-2'-(n-hexyloxy)propyl]imidazole and the antimicrobial acid addition salts thereof.

23. The compound of claim 7 which is 1-[3'-(4''-chlorophenylthio)-2'-(n-heptyloxy)propyl]imidazole and the antimicrobial acid addition salts thereof.

24. The compound of claim 7 which is 1-[2'-(n-butylthio)-3'-(2'',4''-dichlorophenylthio)propyl]imidazole and the antimicrobial acid addition salts thereof.

25. The compound of claim 7 which is 1-[3'-(2'',4''-dichlorophenylthio)-2'-(n-pentylthio)propyl]imidazole and the antimicrobial acid addition salts thereof.

26. The compound of claim 7 which is 1-[3'-(2'',4''-dichlorophenylthio)-2'-(n-pentyloxy)propyl]imidazole and the antimicrobial acid addition salts thereof.

27. The compound of claim 7 which is 1-[3'-(2'',4''-dichlorophenylthio)-2'-(n-hexyloxy)propyl]imidazole and the antimicrobial acid addition salts thereof.

28. The compound of claim 7 which is 1-[3'-(n-butylthio)-2'-(4''-chlorobenzyloxy)propyl]imidazole and the antimicrobial acid addition salts thereof.

29. The compound of claim 7 which is 1-[2'-(4''-chlorobenzyloxy)-3'-(n-pentylthio)propyl]imidazole and the antimicrobial acid addition salts thereof.

30. The compound of claim 7 which is 1-[2'-(4''-chlorobenzyloxy)-3'-(n-hexylthio)propyl]imidazole and the antimicrobial acid addition salts thereof.

31. The compound of claim 7 which is 1-[3'-(n-butylthio)-2'-(2'',4''-dichlorobenzyloxy)propyl]imidazole and the antimicrobial acid addition salts thereof.

32. The compound of claim 7 which is 1-[2'-(2'',4''-dichlorobenzyloxy)-3'-(n-pentylthio)propyl]imidazole and the antimicrobial acid addition salts thereof.

33. The compound of claim 7 which is 1-[2'-(2'',4''-dichlorophenylthio)-3'-(n-propylthio)propyl]imidazole and the antimicrobial acid addition salts thereof.

34. The compound of claim 7 which is 1-[3'-(n-butylthio)-2'-(2'',4''-dichlorophenylthio)propyl]imidazole and the antimicrobial acid addition salts thereof.

35. The compound of claim 7 which is 1-[2'',4''-dichlorophenylthio)-3'-(n-pentylthio)propyl]imidazole and the antimicrobial acid addition salts thereof.

36. A composition useful for inhibiting the growth of fungi, bacteria or protozoa which comprises an effective amount of a compound of the formula

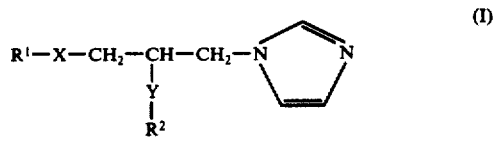

(I)

wherein:
one of $R^1$ and $R^2$ is alkyl having 1 to 12 carbon atoms or the group

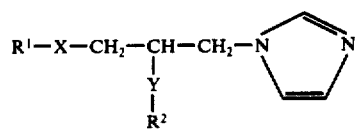

in which $n$ to 0 to 3, and the other of $R^1$ and $R^2$ is benzyl, substituted benzyl, phenyl or substituted phenyl, said substituted benzyl and substituted phenyl substituted on the phenyl ring with one or more substitutents independently selected from the group consisting of halo, lower alkyl and trifluoromethyl;

X and Y are independently oxygen or sulfur with the proviso that Y is not oxygen when $R^2$ is phenyl or substituted phenyl; or an antimicrobial acid addition salt thereof in admixture with a suitable carrier.

37. A composition of claim 36 for pharmaceutical use wherein the carrier is a pharmaceutically acceptable non-toxic carrier.

38. A composition of claim 37 for topical administration wherein the compound of Formula (I) is present in an amount ranging between 0.1 and 10.0 weight percent of the composition.

39. A method of inhibiting the growth of fungi, bacteria or protozoa which comprises applying to a host object containing or subject to attack by fungi, bacteria or protozoa an effective amount of a compound of the formula

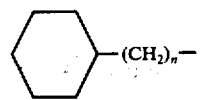

(I)

wherein:
one of $R^1$ and $R^2$ is alkyl having 1 to 12 carbon atoms or the group

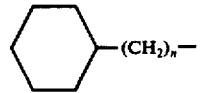

in which $n$ is 0 to 3, and the other of $R^1$ and $R^2$ is benzyl, substituted benzyl, phenyl or substituted phenyl, said substituted benzyl and substituted phenyl substituted on the phenyl ring with one or more substitutents independently selected from the group consisting of halo, lower alkyl and trifluoromethyl;

X and Y are independently oxygen or sulfur with the proviso that Y is not oxygen when $R^2$ is phenyl or substituted phenyl; or an antimicrobial acid addition salt thereof or a composition containing same as an active ingredient.

40. The method of claim 39 wherein the compound of Formula (I) is administered topically.

41. The method of claim 39 wherein the compound of Formula (I) is administered orally or parenternally.

* * * * *